United States Patent
Murray et al.

(10) Patent No.: US 10,076,419 B2
(45) Date of Patent: *Sep. 18, 2018

(54) METHOD OF IMPLANTING A UNICONDYLAR KNEE PROSTHESIS

(71) Applicant: Biomet UK Limited, Bridgend (GB)

(72) Inventors: David Wycliffe Murray, Oxford (GB); Christopher Dodd, Oxford (GB)

(73) Assignee: Biomet UK Limited (GB)

( * ) Notice: Subject to any disclaimer, the term of this patent is extended or adjusted under 35 U.S.C. 154(b) by 221 days.

This patent is subject to a terminal disclaimer.

(21) Appl. No.: 14/881,821

(22) Filed: Oct. 13, 2015

(65) Prior Publication Data
US 2016/0030186 A1 Feb. 4, 2016

Related U.S. Application Data

(63) Continuation of application No. 12/496,099, filed on Jul. 1, 2009, now Pat. No. 9,173,743.

(51) Int. Cl.
*A61B 17/56* (2006.01)
*A61F 2/38* (2006.01)
(Continued)

(52) U.S. Cl.
CPC .......... *A61F 2/3868* (2013.01); *A61B 17/155* (2013.01); *A61B 17/157* (2013.01);
(Continued)

(58) Field of Classification Search
CPC ................ A61B 17/157; A61B 17/155; A61B 2017/564; A61F 2002/3895
See application file for complete search history.

(56) References Cited

U.S. PATENT DOCUMENTS

| | | |
|---|---|---|
| 4,224,696 A | 9/1980 | Murray et al. |
| 4,309,778 A | 1/1982 | Buechel et al. |
| (Continued) | | |

FOREIGN PATENT DOCUMENTS

| | | |
|---|---|---|
| DE | 202008005407 U1 | 9/2008 |
| JP | 58048180 B2 | 10/1983 |
| (Continued) | | |

OTHER PUBLICATIONS

"U.S. Appl. No. 12/496,099, Examiner Interview Summary dated Jan. 9, 2012", 3 pgs.
(Continued)

*Primary Examiner* — Brian Pellegrino
(74) *Attorney, Agent, or Firm* — Schwegman Lundberg & Woessner, P.A.

(57) ABSTRACT

A method of implanting a lateral unicondylar knee prosthesis in a lateral articulating portion of a femur having a lateral condyle for engagement with a tibia, the method including the steps of: bending a patients knee such that the knee is not in full extension; making an incision through the skin, muscle, and other soft tissue until the damaged bone surfaces are exposed; resecting an end portion of the lateral tibia; resecting an end portion of the lateral femoral condyle; attaching a tibial prosthetic component to the resected end portion of the tibia; attaching a lateral femoral condyle prosthetic component to the resected end portion of the lateral femoral condyle; determining the thickness of a mobile bearing member with the knee in full extension; and inserting the mobile bearing member between the tibial prosthetic component and the femoral prosthetic component.

19 Claims, 12 Drawing Sheets

(51) Int. Cl.
  *A61B 17/15* (2006.01)
  *A61B 17/17* (2006.01)
  *A61F 2/46* (2006.01)
  *A61F 2/30* (2006.01)

(52) U.S. Cl.
  CPC ............ *A61B 17/1764* (2013.01); *A61F 2/38* (2013.01); *A61F 2/461* (2013.01); *A61F 2/4684* (2013.01); *A61F 2/30965* (2013.01); *A61F 2002/3895* (2013.01); *A61F 2240/001* (2013.01); *A61F 2310/00017* (2013.01); *A61F 2310/00023* (2013.01); *A61F 2310/00029* (2013.01); *A61F 2310/00095* (2013.01); *A61F 2310/00179* (2013.01)

(56) References Cited

U.S. PATENT DOCUMENTS

| | | | |
|---|---|---|---|
| 5,358,530 | A | 10/1994 | Hodorek |
| 5,735,904 | A | 4/1998 | Pappas |
| 6,149,687 | A | 11/2000 | Gray et al. |
| 9,173,743 | B2 | 11/2015 | Murray et al. |
| 2002/0198530 | A1 | 12/2002 | Sanford et al. |
| 2003/0028196 | A1* | 2/2003 | Bonutti ................ A61B 17/155 606/87 |
| 2003/0055500 | A1* | 3/2003 | Fell ....................... A61F 2/3868 623/14.12 |
| 2004/0006394 | A1 | 1/2004 | Lipman et al. |
| 2004/0153086 | A1 | 8/2004 | Sanford |
| 2004/0153087 | A1 | 8/2004 | Sanford et al. |
| 2005/0216090 | A1 | 9/2005 | O'driscoll et al. |
| 2006/0195195 | A1 | 8/2006 | Burstein et al. |
| 2007/0005142 | A1 | 1/2007 | Rhodes et al. |
| 2007/0173946 | A1 | 7/2007 | Bonutti |
| 2011/0004316 | A1 | 1/2011 | Murray et al. |

FOREIGN PATENT DOCUMENTS

| | | |
|---|---|---|
| JP | 09276304 A | 10/1997 |
| JP | 09289997 A | 11/1997 |
| JP | 2007075517 A | 3/2007 |
| JP | 2009513187 A | 4/2015 |
| WO | WO-2007041375 A2 | 4/2007 |
| WO | WO-2007108933 A1 | 9/2007 |

OTHER PUBLICATIONS

"U.S. Appl. No. 12/496,099, Examiner Interview Summary dated Jun. 18, 2015", 3 pgs.

"U.S. Appl. No. 12/496,099, Final Office Action dated Aug. 29, 2012", 21 pgs.

"U.S. Appl. No. 12/496,099, Non Final Office Action dated Dec. 21, 2011", 16 pgs.

"U.S. Appl. No. 12/496,099, Notice of Allowance dated Jun. 26, 2015", 10 pgs.

"U.S. Appl. No. 12/496,099, Response filed dated Feb. 28, 2013 to Final Office Action dated Aug. 29, 2012", 22 pgs.

"U.S. Appl. No. 12/496,099, Response filed Jun. 21, 2012 to Non Final Office Action dated Dec. 21, 2011", 21 pgs.

"U.S. Appl. No. 12/496,099, Response filed Sep. 23, 2011 to Restriction Requirement dated Jun. 30, 2011", 9 pgs.

"U.S. Appl. No. 12/496,099, Restriction Requirement dated Jun. 30, 2011", 8 pgs.

"International Application Serial No. PCT/GB2010/051077, International Search Report dated Dec. 7, 2010", 5 pgs.

"International Application Serial No. PCT/GB2010/051077, Written Opinion dated Dec. 7, 2010", 6 pgs.

"Japanese Application Serial No. 2012-518131, Office Action dated May 5, 2014", 5 pgs.

"Japanese Application Serial No. 2012-518131, Office Action dated Nov. 4, 2014", 5 pgs.

* cited by examiner

METHOD OF IMPLANTING A UNICONDYLAR KNEE PROSTHESIS

FIELD OF THE INVENTION

The present invention relates to a method for knee surgery, and in particular, to a method of implanting a unicondylar knee prosthesis.

BACKGROUND OF THE INVENTION

The knee joint is where the end of the upper leg bone (femur) meets the top of the lower leg bone (tibia). The end of the femur consists of two condyles, which are like runners or wheels on each side of the bone that both roll and slide with respect to the other surface. These condyles are located on top of the tibia, which is like a platform that is slightly dished on the medial side but slightly convex on the lateral side. Thus, on each side of the joint, there is an area of contact between the two bones. When the knee is bent, the condyles of the femur roll and slide on top of the tibia at these two areas of contact. A third bone, the kneecap (patella), glides over the front and end of the femur.

The two condyles form two articular bodies of the femur and are respectively named its lateral (outer) and medial (towards the middle) condyles. These diverge slightly distally (front) and posteriorly (rear), with the lateral condyle being wider in front than at the back while the medial condyle is of more constant width. The radius of the condyles' curvature in the sagittal plane becomes smaller toward the back. This diminishing radius produces a series of involute midpoints (i.e. located on a spiral). The resulting series of transverse axes (along the involute midpoints) permit the sliding and rolling motion in the flexing knee while ensuring the collateral ligaments are sufficiently lax to permit the rotation associated with the curvature of the medial condyle about a vertical axis.

Motion of a natural knee is kinematically complex. During a relatively broad range of flexion and extension, the articular or bearing surfaces of a natural knee experience rotation, medial and lateral angulation, translation in the sagittal plane, rollback and sliding. The knee joint, in combination with ligaments and muscles, attempt to produce this complex knee motion, as well as absorb and control forces generated during the range of flexion.

In a healthy knee joint, the surfaces of these bones are very smooth and covered with a tough protective tissue called cartilage. Arthritis causes damage to one or more of the bone surfaces and cartilage where the bones rub together. In particular, osteoarthritis or "wear-and-tear" arthritis is a condition where the surface of the joint is damaged and the surrounding bone grows thicker, as a result of bone against bone friction. This friction can cause severe pain and eventually loss of movement.

One option for treating the permanent deterioration of the cartilage is total knee replacement surgery. In a total knee replacement procedure the end surfaces of the tibia and femur, and the posterior surface of the patella, are resurfaced. Generally, the surface that covers the femoral section is made from smooth metal or ceramic, while the surface attached to the tibia is constructed of metal and a high-density polyethylene. The patella is also resurfaced with a high-density polyethylene.

While known knee joint prostheses have proven to be effective in replacing the anatomical knee joint, they nevertheless have several disadvantages. For example, knee joint prostheses sometimes lack adaptability to implant conveniently with a given patient. In this regard, in a normally shaped femur, the central canal is typically offset from the centre of the femoral articulating surfaces. Furthermore, the central femoral canal may present various valgus angles from one patient to another.

In some cases, there may be significant damage on only one side of the joint or to only one of the condyles. In these cases, a partial (unicompartmental) knee replacement may be considered. In a partial knee replacement, only one side of the joint is resurfaced.

Accordingly, it is desirable to develop a method for knee surgery, and in particular, a method of implanting a unicondylar knee prosthesis which may help make surgery, recovery, and rehabilitation faster and easier for the patient and that seeks to preferably mitigate, alleviate or eliminate one or more of the disadvantages mentioned above singly or in any combination.

Any discussion of documents, acts or knowledge in this specification is included to explain the context of the invention. It should not be taken as an admission that any of the material forms part of the prior art base or the common general knowledge in the relevant art.

SUMMARY OF THE INVENTION

According to a first aspect, the present invention provides a method of implanting a lateral unicondylar knee prosthesis in a lateral articulating portion of a femur having a lateral condyle for engagement with a tibia, the method comprising the steps of: bending a patients knee such that the knee is not in full extension; making an incision through the skin, muscle, and other soft tissue until the damaged bone surfaces are exposed; resecting an end portion of the lateral tibia; resecting an end portion of the lateral femoral condyle; attaching a tibial prosthetic component to the resected end portion of the tibia; attaching a lateral femoral condyle prosthetic component to the resected end portion of the lateral femoral condyle; determining the thickness of a mobile bearing member with the knee in full extension; and inserting the mobile bearing member between the tibial prosthetic component and the femoral prosthetic component.

The position of the lateral femoral condyle may be determined anatomically with reference to the femur. The step of resecting the end portion of the tibia may comprise sawing vertically a cut through the centre of a patella tendon positioned in line with the medial side of the lateral femoral condyle; and sawing horizontally a cut that removes bone to accommodate the tibial prosthetic component and the mobile bearing member with the knee in full extension. Sawing horizontally may further comprise removing bone to approximately 8 mm below the original tibial articular surface or 2 to 3 mm below the eburnated bone of the tibia. The tibial prosthetic component may include a smooth articular surface and a bone-contacting surface opposite the articular surface. The smooth articular surface may be formed in a convex shape. The bone-contacting surface opposite the articular surface may further include a projection extending from the bone-contacting surface. The step of attaching the tibial prosthetic component may include resecting the bone to accommodate the projection extending from the bone-contacting surface; and cementing the tibial prosthetic component to the tibia. The step of attaching the tibial prosthetic component may include resecting the bone to accommodate the projection extending from the bone-contacting surface; and attaching a cementless tibial prosthetic component to the tibia. The step of resecting the end portion of the lateral femoral condyle may include drilling a hole in a notch between the lateral femoral condyle and the medial femoral condyle to accommodate an intramedullary rod; inserting a lateral femoral drill guide; adjusting the leg and the lateral femoral drill guide to be parallel to the intramedullary rod; drilling two holes through the lateral femoral drill guide; attaching a posterior saw guide to the lateral femoral compartment; and milling the bone from the lateral femoral condyle in both anterior and posterior directions. The femoral prosthetic component may include a smooth articular surface and a bone-contacting surface opposite the articular surface. The smooth articular surface may be formed in a convex shape. The bone-contacting surface opposite the articular surface may further include a spigot extending from the bone-contacting surface. The step of attaching the lateral femoral prosthetic component may include cementing the lateral femoral prosthetic component to the femur. The step of attaching the lateral femoral prosthetic component may include attaching a cementless lateral femoral prosthetic component to the femur. The mobile bearing member may be a biconcave bearing having a first bearing surface that articulates with the smooth articular surface of the tibial prosthetic component and a second bearing surface that articulates with the smooth articular surface of the femoral prosthetic component. The tibial prosthetic component, the femoral prosthetic component and the mobile bearing member may be made of a material selected from the group of titanium, titanium alloy, cobalt chrome alloy, ceramic, biocompatible composite, polymer, niobium, and steel alloy.

According to a further aspect, the present invention provides a method of implanting a lateral unicondylar knee prosthesis in a lateral articulating portion of a femur having a lateral condyle for engagement with a tibia, the method including the steps of: bending a patients knee such that the knee is not in full extension; making an incision through the skin, muscle, and other soft tissue until the damaged bone surfaces are exposed; resecting an end portion of the lateral tibia; sizing a tibial template component by fully extending the knee; resecting an end portion of the lateral femoral condyle; sizing a lateral femoral template component by fully extending the knee; and sizing a mobile bearing template member for insertion between the tibial template component and the lateral femoral template component.

The position of the lateral femoral condyle may be determined anatomically with reference to the femur. The step of resecting the end portion of the tibia may include sawing vertically a cut through the centre of a patella tendon positioned in line with the medial side of the lateral femoral condyle; and sawing horizontally a cut that removes bone to accommodate the tibial prosthetic component and the mobile bearing member with the knee in full extension. Sawing horizontally may further include removing approximately 8 mm below the original tibial articular surface or 2 to 3 mm below the eburnated bone of the tibia. The tibial template component may include a smooth articular surface and a bone-contacting surface opposite the articular surface. The smooth articular surface may be formed in a convex shape. The step of resecting the end portion of the lateral femoral condyle may include drilling a hole in a notch between the lateral femoral condyle and the medial femoral condyle to accommodate an intramedullary rod; inserting a lateral femoral drill guide; adjusting the leg and the lateral femoral drill guide to be parallel to the intramedullary rod; drilling two holes through the lateral femoral drill guide; attaching a posterior saw guide to the lateral femoral compartment; and milling the bone from the lateral femoral condyle in both anterior and posterior directions. The lateral femoral template component may include a smooth articular surface and a bone-contacting surface opposite the articular surface. The smooth articular surface may be formed in a convex shape. The bone-contacting surface opposite the articular surface further may include a spigot extending from the bone-contacting surface. The method may further include replacing the tibial template component by inserting a tibial prosthetic component; replacing the lateral femoral template component by inserting a lateral femoral condyle prosthetic component; and replacing the mobile bearing template member by inserting a mobile bearing member. A final assessment of the implant of the lateral unicondylar knee prosthesis may be performed and the tibial prosthetic component and the femoral prosthetic component are cemented into their respective bones. A final assessment of the implant of the lateral unicondylar knee prosthesis may be performed and the tibial prosthetic component and the femoral prosthetic component are attached to their respective bones using cementless technology. The mobile bearing member may be a biconcave bearing having a first bearing surface that articulates with the smooth articular surface of the tibial prosthetic component and a second bearing surface that articulates with the smooth articular surface of the femoral prosthetic component. The tibial prosthetic component and the tibial prosthetic template component, the femoral prosthetic component and the femoral prosthetic template component, and the mobile bearing member and the mobile bearing template member may be made of a material selected from the group of titanium, titanium alloy, cobalt chrome alloy, ceramic, biocompatible composite, polymer, niobium, and steel alloy.

According to a still further aspect, the present invention provides a kit for a lateral unicondylar knee prosthesis housed in a sterilisation case, the kit including: a set of femoral components including: at least one femoral drill guide; at least one femoral prosthetic component; at least one femoral prosthetic template component; a femoral instrument set; a set of tibial components including: at least one tibial prosthetic component; at least one tibial prosthetic template component; a tibial impactor; a tibial instrument set; a set of bearing components including: at least one mobile bearing member; at least one mobile bearing template member; a bearing insert/removal tool; a set of feeler gauges for determining correct sizing of components; and a set of instructions for performing a lateral unicondylar knee implant surgery.

The tibial prosthetic component and the femoral prosthetic component may be cemented into their respective bones. The tibial prosthetic component and the femoral prosthetic component may be attached to their respective bones using cementless technology. The tibial prosthetic component and the tibial prosthetic template component, the femoral prosthetic component and the femoral prosthetic template component, and the mobile bearing member and the mobile bearing template member may be made of a material selected from the group of titanium, titanium alloy, cobalt chrome alloy, ceramic, biocompatible composite, polymer, niobium, and steel alloy.

The present invention provides a partial knee replacement procedure that not only helps the knee joint function better but has also proven to improve both recovery and rehabilitation after surgery. The procedure involves removing only the diseased portion of the knee, traditional total knee replacement surgery involves removing or resurfacing more parts of the knee, including both condyles and often the underside of the kneecap.

The present invention is a less invasive approach to knee surgery and is particularly suited to patients who are still in the early stages of osteoarthritis. This means only the parts (the medial, 'inner' compartment or lateral 'outer' compartment) of the knee that have been damaged by the disease need replacing, therefore avoiding having to undergo a total knee replacement. This procedure preserves the healthy parts of the joint, as it only replaces one side of the knee, leading to an artificial joint with a function that is closer to the natural knees movements.

The component parts of the prosthesis have been designed to have surfaces that fit one another in all positions such that the kinematically complex movements of the knee are retained. This also means that component parts of the prosthesis wear out very slowly. A further benefit of this procedure is that by retaining all the undamaged parts, in particular the cruciates and ligaments, the joint bends better and has a more natural function.

These and other objects, along with the advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. In addition, the drawings are not necessarily to scale, emphasis instead generally being placed upon illustrating the principles of the invention. In the following description, various embodiments of the present invention are described with reference to the following drawings, in which.

DETAILED DESCRIPTION

The present invention will be discussed hereinafter in detail in terms of various embodiments of a method of implanting a unicondylar knee prosthesis. In the following description, numerous specific details are set forth in order to provide a thorough understanding of the present invention. It will be obvious, however, to those skilled in the art that the present invention may be practiced without these specific details.

Figure 1:
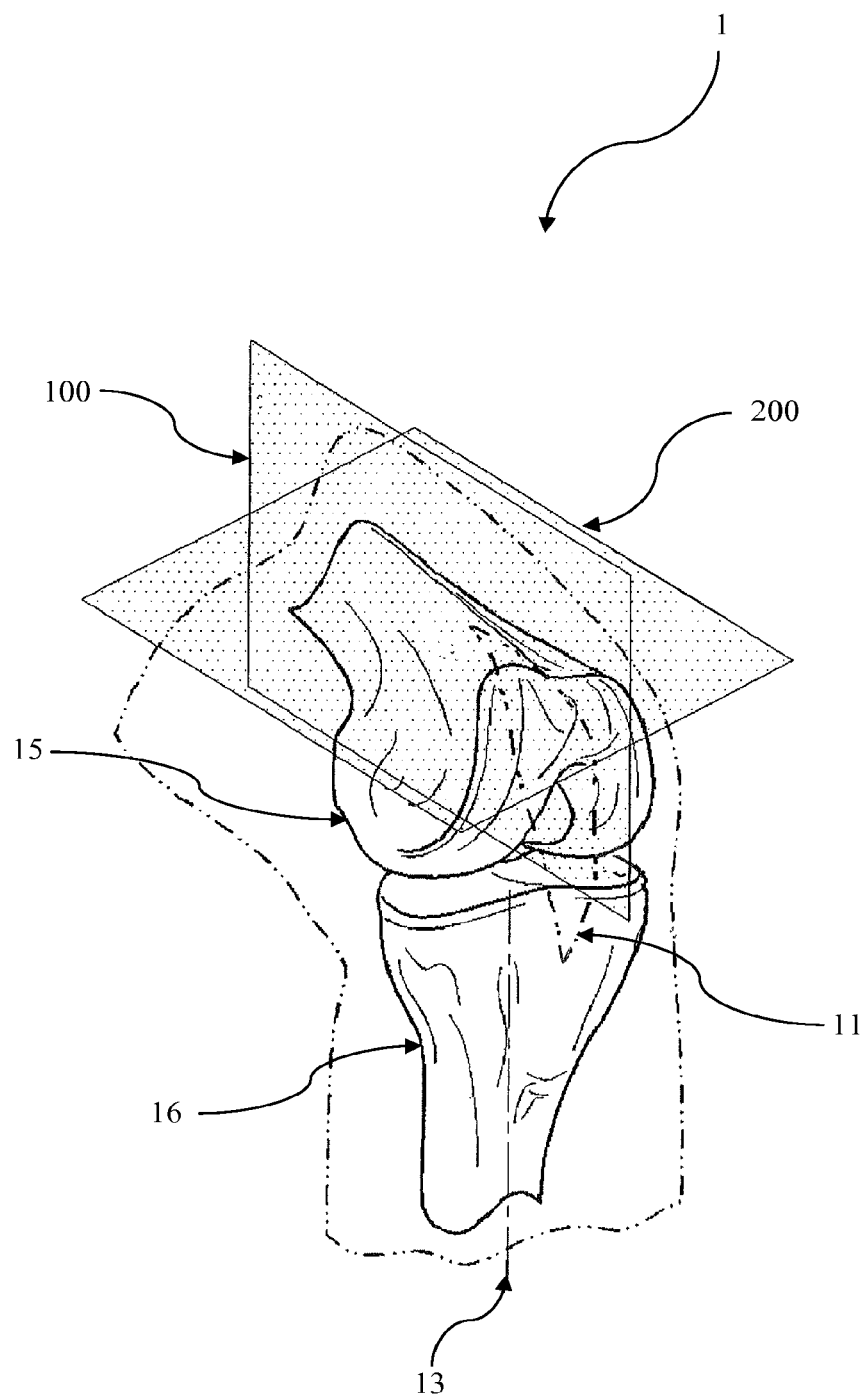
FIG. 1 is a perspective view of the knee joint, without the muscle and connective tissue, showing a lateral condyle and a medial condyle of the femur in accordance with the present teachings, and also showing reference planes with respect to the knee joint.

With reference to FIG. 1, it will be appreciated that the anterior-posterior plane 100 and the medial-lateral plane 200 are not exactly and specifically located on the body but can provide general guidance as to orientation and location. As such, alignment of the prosthetic 20 (FIG. 3) to the anterior-posterior plane 100 and the spigot (not shown) of the femoral component 30 and the femur 15 to the medial-lateral plane 200 can provide a general orientation of the femoral component 30 relative to the femur 15 and the tibia 16. Also shown in FIG. 1 is the line 13 that defines a longitudinal axis of the tibia 16.

With reference to FIG. 1, the incision 11 (or multiple incisions) can be made at various locations around the knee joint 1 and can aid in insertion of the femoral component 30 and/or the tibial component 40. While a minimally invasive incision can be used, the femoral component 30 and/or the tibial component 40 can be compatible with other incisions and/or other suitable medical equipment.

Figures 2A, 2B:
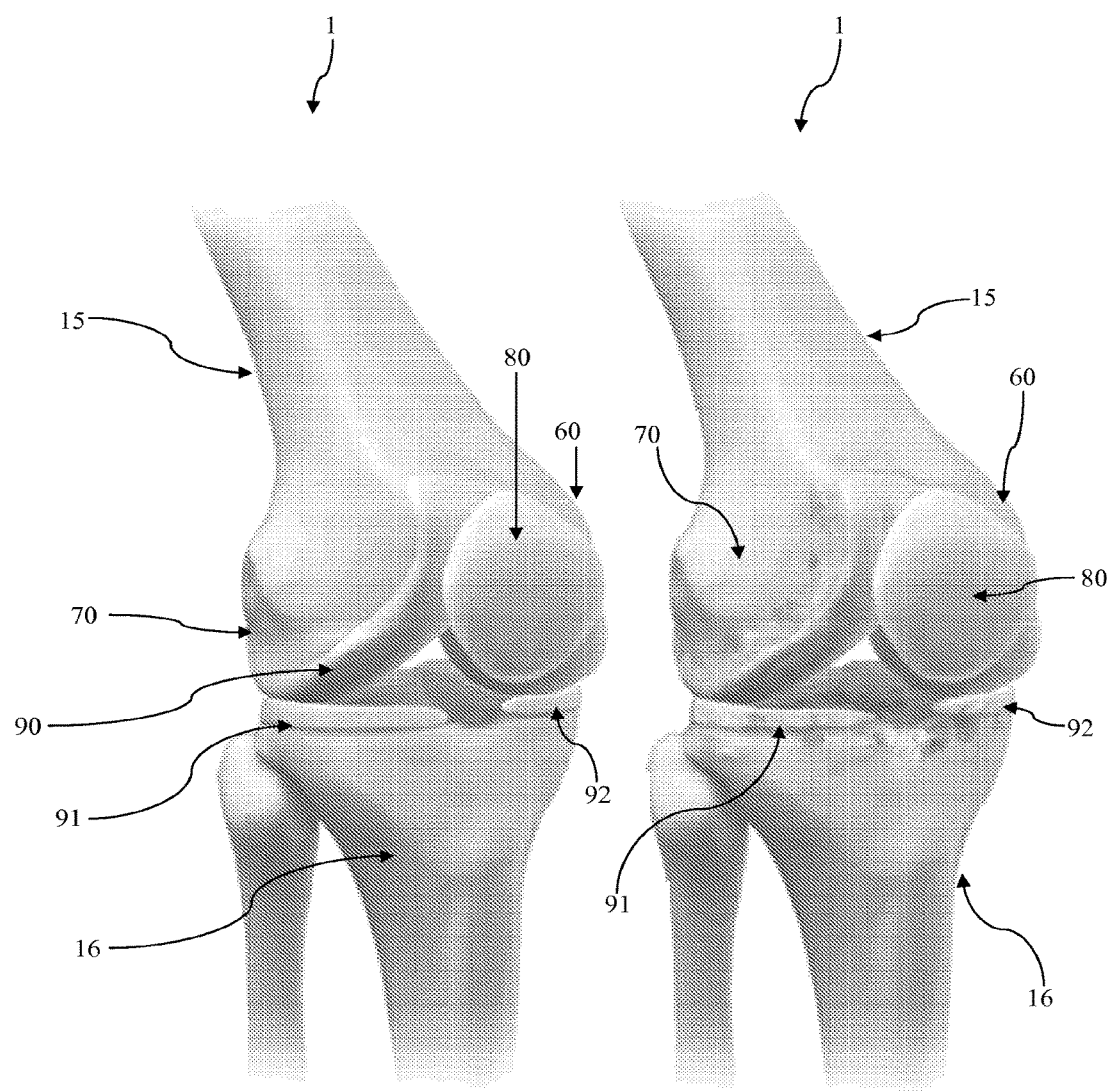
FIG. 2a is a perspective view of the knee joint showing a healthy knee joint.
FIG. 2b is a perspective view of a knee joint showing progressive knee joint degeneration that may be due to osteoarthritis.

FIG. 2a shows a healthy knee joint 1 and FIG. 2b shows a knee joint showing progressive knee joint degeneration. The knee joint 1 is where the end of the femur 15 meets the top of the tibia 16. The end of the femur 15 consists of two condyles 60, 70. These condyles 60, 70 sit on top of the tibia 16, which is like a platform that is slightly dished on each side. Thus, on each side of the joint 1, there is an area of contact between the two bones. When the knee is bent, the condyles 60, 70 of the femur 15 roll and slide on top of the tibia 16 at these two areas of contact. A third bone, the kneecap (patella) 80, glides over the front and end of the femur 15.

In a healthy knee joint (FIG. 2a), the surfaces of these bones are very smooth and covered with cartilage—a tough protective tissue. The articular disks of the knee-joint are called menisci 91, 92 because they only partly divide the joint space. These two disks, the medial meniscus 91 and the lateral meniscus 92, consist of connective tissue with extensive collagen fibers containing cartilage-like cells. Strong fibers run along the menisci 91, 92 from one attachment to the other, while weaker radial fibers are interlaced with the former. The menisci 91, 92 are flattened at the centre of the knee joint, fused with the synovial membrane laterally, and can move over the tibial surface 16. Also in a healthy knee joint is the articular cartilage 90, also called hyaline cartilage, which is the smooth, glistening white tissue that covers the surface of all the diarthrodial joints in the human body.

The menisci 91, 92 serve to protect the ends of the bones from rubbing on each other and to effectively deepen the tibial sockets into which the femur 15 attaches.

They also play a role in shock absorption, and may be cracked, or torn, when the knee is forcefully rotated and/or bent. FIG. 2b shows a knee joint 1 which arthritis has caused damage to one or more of the bone surfaces and cartilage where the bones rub together. In particular, osteoarthritis is a condition where the surface of the joint is damaged and the surrounding bone grows thicker, resulting in bone against bone friction. This friction can cause severe pain and eventually loss of movement. In some cases, there may be significant damage on only one side of the joint 1 or to only one of the condyles 60, 70. In these cases, a partial (uni-compartmental) knee replacement may be considered. In a partial knee replacement, only one side of the joint 1 is resurfaced.

Up until now, surgeons have used the same techniques to replace the lateral condyle 60 as they have used to replace the medial condyle 70. It has not previously been appreciated that better results are obtained by using a different operative procedure for the lateral condyle 60. By better results, we mean fewer problems post-operative, less pain and recovery and rehabilitation is faster and easier for the patient, reduction of bearing dislocation, improved range of movement and improved kinematics of the knee.

It has now been appreciated that the different forces and motion experienced in use by medial and lateral condylar 60, 70 replacement inserts can be better achieved by fitting the lateral condylar 60 replacement differently from how the medial condylar 70 replacement is fitted. In particular, sizing the lateral condylar 60 replacement insert with the leg fully extended (straight) is better, despite not being what is done for medial condylar 60 replacement. It is somewhat counterintuitive to size the insert whilst the knee 1 is straight—the exterior ligament is slack in this position, and sizing the insert with a slack ligament may instinctively feel wrong, but it is better.

The present invention has been developed for the above case where only one side of the joint 1 or one of the condyles 60, 70 has been damaged. The method for knee surgery, and in particular, a method of implanting a lateral unicondylar knee prosthesis 20 has been developed to make surgery, recovery, and rehabilitation faster and easier for the patient.

Figure 3:
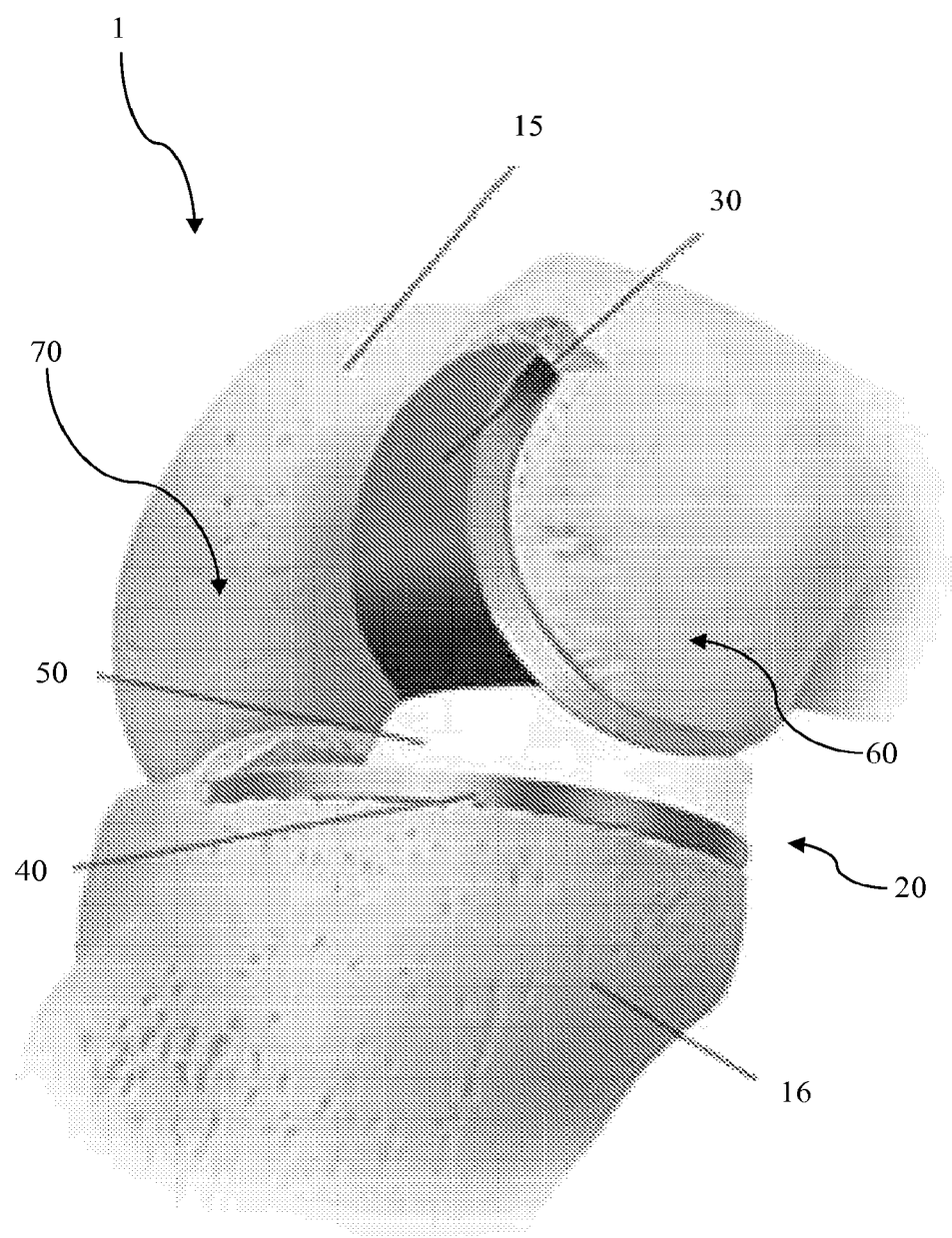
FIG. 3 is a perspective view of a knee showing a femoral component secured to the lateral condyle and a tibial component implanted over the lateral articular surface of the tibia and a mobile bearing in accordance with the present invention.

The procedure and reasoning for a lateral unicondylar partial knee implant will now be described with reference to FIG. 3. FIG. 3 shows a perspective view of a knee 1 showing a femoral component 30 secured to the lateral condyle 60 and a tibial component 40 implanted over the lateral articular surface of the tibia 16. A mobile bearing member 50 is inserted between the tibial prosthetic component 40 and the femoral prosthetic component 30. Further detail of the tibial component 40 will be described below with reference to FIG. 4, the femoral prosthetic component 30 will be described with reference to FIG. 5 and the mobile bearing member 50 will be described with reference to FIG. 6.

There are many differences between the medial and lateral compartments of the knee 1. One of the most important is that in flexion, the lateral collateral ligament (LCL) is slack whereas the medial collateral ligament (MCL) is tight. Therefore, it is not possible to determine the position of the lateral femoral condyle 60 from ligament balance, as is done in operations to replace the medial compartment (discussed in more detail latter). Also, isolated lateral arthritis is a disease of flexion and tends to be maximal at 40° flexion. It is therefore different from medial osteoarthritis, which is a disease of extension.

Instead, an aim of one aspect of the present invention is to position the component 20 anatomically. This is possible because in lateral osteoarthritis there is usually little damage to the femur 15 at 90° flexion (or thereabouts) and in full extension (or thereabouts), so the femoral component 30 can be positioned with reference to these surfaces. Once the tibial 40 and femoral 30 components are implanted, the appropriate mobile bearing 50 is selected in full extension, when the LCL is tight, thus restoring leg alignment to the predisease situation. Selecting the mobile bearing 50 with the knee in extension, rather than flexed, as with a medial unicondylar replacement, is another difference.

Figure 4:
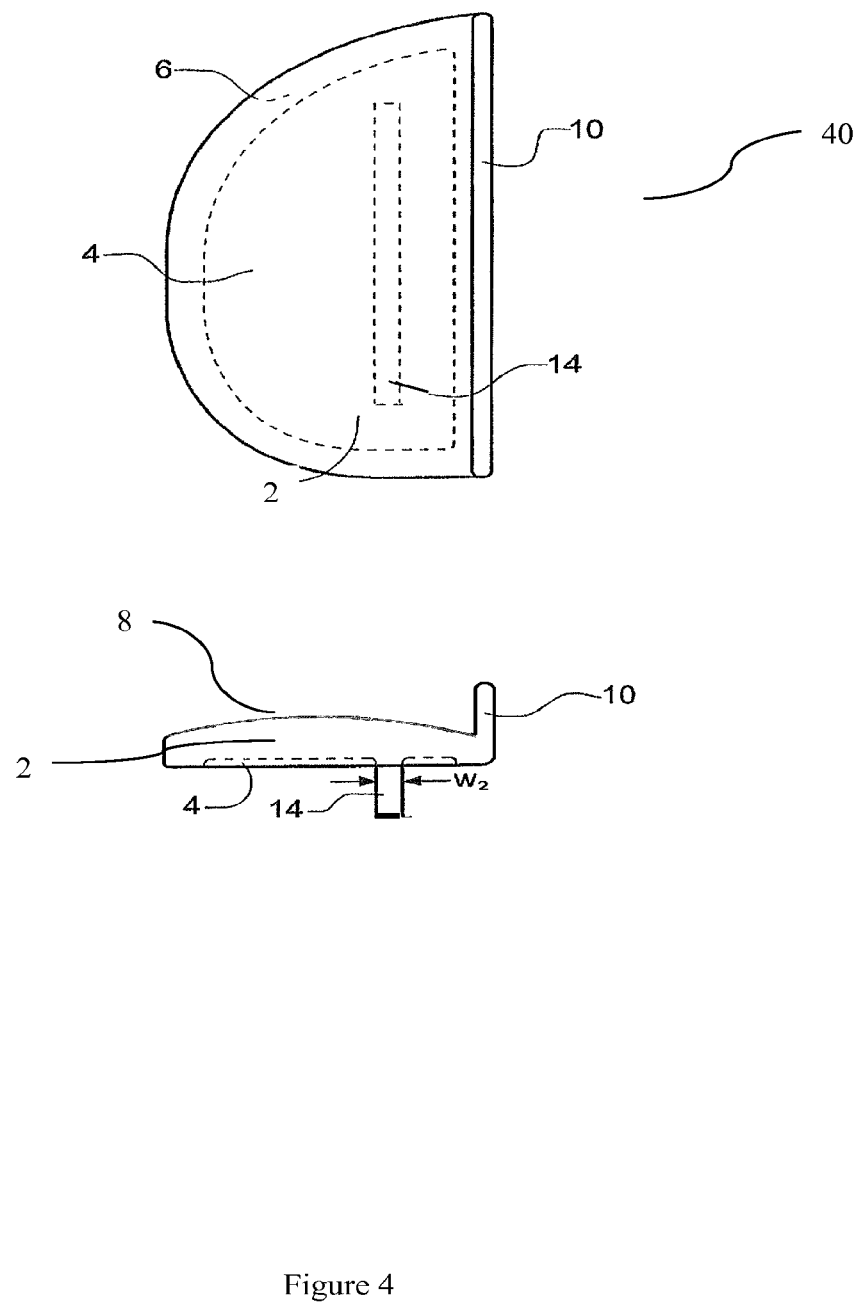
FIG. 4 is a schematic view of a tibial component in accordance with the present invention.

FIG. 4 shows the tibial component 40 used to replace a single condylar-bearing portion of a human tibia 16. The tibial component 40 includes a body portion 2 having a substantially flat bone-engaging region 4 that has a raised border disposed around its periphery defining a bone engaging surface 6. The body portion 2 provides a domed articular surface 8 having an abutment 10 projecting therefrom. In use the domed articular surface 8 supports a meniscal or mobile bearing component 50 for engagement with a prosthetic femoral component 30 in such a manner as to enable the prosthesis to serve as a replacement for the natural tibial articular surface and to restore substantially normal anatomical movement of the femur 15 and tibia 16. As is well known in the art the abutment 10 aids to prevent dislocation of the mobile bearing component 50 towards the cruciate ligaments.

The body portion 2 is fixed to the tibia by means of an elongate flange or keel 14 that is anchored directly in the tibia 16. The flange 14 is connected to the bone-engaging region 4 of the body portion 2. In order to implant the prosthesis, a hole of a diameter substantially equal to the width $w_2$ of the flange 14, is drilled into the already resected portion of the tibia 16.

The end of the flange 14 is inserted into the hole and the tibial component 40 prosthesis is driven across the flat surface formed on the tibia 16 until the entire flange 14 is anchored in the tibia 16. Prior to insertion of the flange 14 into the tibia 16, bone cement may be applied to the bone-engaging region 4.

The femoral prosthetic component 30, the tibial prosthetic component 40 and the mobile bearing member 50 are typically constructed of biomaterials that are compatible with use in the body. Some examples of biomaterials include titanium, titanium alloy, cobalt-chrome, cobalt chrome alloy, ceramics, biocompatible composites, polymers including polyethylene, steel alloys, niobium and Trabecular Metal™ material. Niobium is typically used in patients who are metal sensitive. The preferred material for the mobile bearing component 50 is high-density polyethylene, which provides the articular surface with the appropriate lubricity characteristics for the proper functioning of the knee prosthesis 20.

Figure 5:
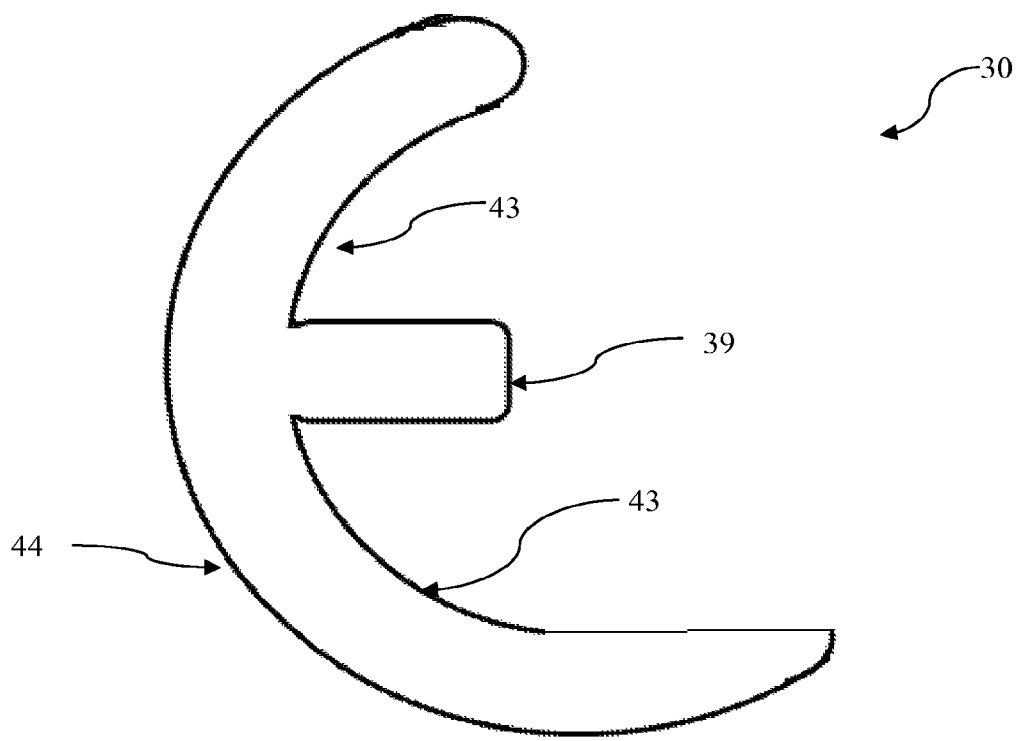
FIG. 5 is a schematic view of a lateral femoral condylar component in accordance with the present invention.

FIG. 5 shows a lateral femoral condylar component 30 having a spigot 39 and lateral femoral engaging surfaces 43 to engage the lateral femoral condyle 60. The body portion provides a domed articular surface 44. In use the domed articular surface 44 supports a meniscal or mobile bearing component 50 for engagement with a prosthetic tibial component 40 in such a manner as to enable the prosthesis to serve as a replacement for the natural femoral articular surface and to restore substantially normal anatomical movement of the femur 15 and tibia 16.

As described above the LCL is slack in flexion therefore the lateral compartment can readily and easily be pulled apart or distracted. Bending the leg so as to make the LCL slack is a part of many embodiments of the invention. Therefore the surgery can be carried out with the leg/knee at any angle provided the leg is not fully extended. That means in some embodiments at any angle within the range of approximately 10 degrees to 90 degrees (or perhaps more) flexion. In some embodiments a preferred range of knee bend is between 20 degrees and about 90 degrees (say 90 degrees plus or minus 5 or 10 degrees), or between 30, or 40, or 50, or 60, or 70, or 80 degrees, and about 90 degrees. Bending the knee whilst fitting the unicondylar lateral implant causes a higher risk of dislocation of the bearing implant 50 laterally than medially. In order to prevent this dislocation, in many embodiments a biconcave bearing 50 (FIG. 6) is implanted between the femoral component 30 and the tibial component 40 which enhances entrapment and therefore aids in the prevention of dislocation.

Figure 6:
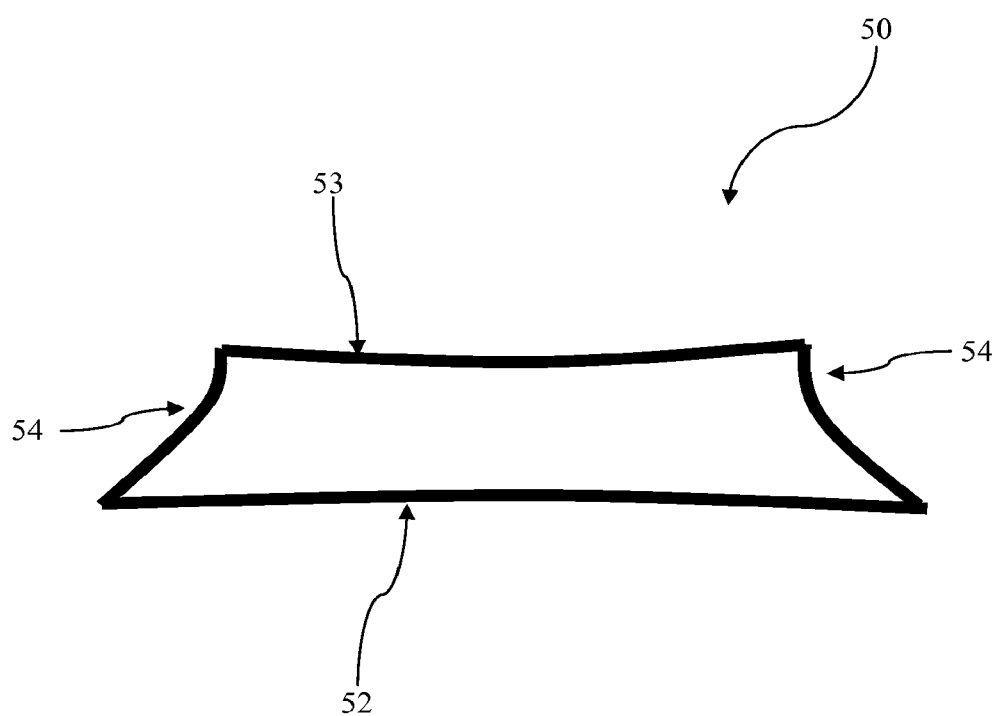
FIG. 6 is a schematic view of a biconcave bearing member in accordance with the present invention.

A biconcave bearing 50 is essentially required due to the lateral tibial plateau (articulating surface) being convex or more of a D-shape than the medial plateau. This is mirrored in the shape of the components used for the bearing 50. As shown in FIG. 6, the top and bottom surfaces 52, 53 of the mobile bearing 50 are concave shaped to mirror the shapes of the lateral tibial plateau and the lateral femoral condyle 60. The two concave surfaces 52, 53 or outer faces are curved inward and are joined by the surface 54 surrounding the bearing 50.

Although the lateral femoral condyle 60 is more circular in the sagittal plane than the medial, it is less circular in cross section, which can be disorientating. The patella 80 and patella tendon lie in front of the lateral femoral condyle 60, which also makes access difficult. Another consideration, which should be observed, is the popliteus (a thin, flat, triangular muscle at back of the knee, the action of which assists in bending the knee and in rotating the leg toward the body) may bowstring across the back of the lateral compartment and cause mobile bearing 50 dislocation.

During flexion and extension, there is a large amount of movement of the lateral femoral condyle 60 on the tibia 16. In high flexion the mobile bearing 50 overhangs the back of the tibial component 40. Therefore, the back of the knee 1 has to be free of obstructions. As the knee 1 extends, as well as moving forwards the mobile bearing 50 moves medially so the tibial component 40 has to be markedly internally rotated.

The procedure for implanting a prosthetic knee 20 to the lateral femoral condyle 60 is broadly similar to that of implanting a prosthetic knee 20 to the medial femoral condyle 70 and will be described with reference to FIGS. 7 to 13. An incision 11 is made over the junction between the central and lateral third of the patella 80. It starts about 2 cm above the patella 80 and ends just below and lateral to the tibial tuberosity. The retinaculum is incised lateral to the patella 80 and the ligamentum patellae. The retinacular incision is extended upwards into the quadriceps tendon to allow the patella 80 to sublux medially.

As described above the patella 80 and patella tendon are in front of the lateral femoral condyle 60 making access to the lateral compartment difficult. Occasionally it is necessary to remove a strip of bone 5 to 7 mm wide from the lateral side of the patella 80 to gain adequate exposure. Generous excision of the fat pad, particularly in the intercondylar notch 33, is necessary to gain adequate access.

The next step in the procedure is to inspect the joint 1 and assess the state of the anterior cruciate ligament, the patello femoral joint and the medial compartment. If any of these are in a poor state, a total knee replacement would be required rather than a unicondylar replacement. Osteophytes (a small, abnormal bony outgrowth) are then removed along with the removal of the lateral notch osteophytes and care is taken to define the medial border of the lateral femoral condyle 60.

The next step is to resect the tibial plateau. Starting with the tibia 16, the patella tendon is exposed and its lower portion is split centrally, for example with a knife. A vertical saw cut is made through the patella tendon with the knee flexed to 90°. The saw blade should touch the medial side of the lateral condyle 60. The two landmarks, the centre of the tendon and the medial side of the lateral condyle 60 define the position of the cut and ensure it is adequately internally rotated. The saw cut will usually be at the correct depth when its upper edge is level with the bone surface.

The lateral tibial resection guide is applied in a manner similar to that used on the medial side. For example, the lateral tibial resection guide would be strapped around the ankle and adjusted to be parallel to the tibial crest. It should be positioned parallel to the vertical saw cut. The aim is for the horizontal is to remove sufficient bone to accommodate the tibial prosthetic component 40 and the mobile bearing member 50 with the knee in full extension. This is achieved by making a horizontal saw cut to a depth of approximately 8 mm below the original tibial articular surface. If the site of the original surface can not be estimated, the cut should be approximately 2 or 3 mm below the eburnated bone. As the domed tibial component is thicker than the flat medial component, the lateral tibial resection should be thicker than the medial.

Figure 7:
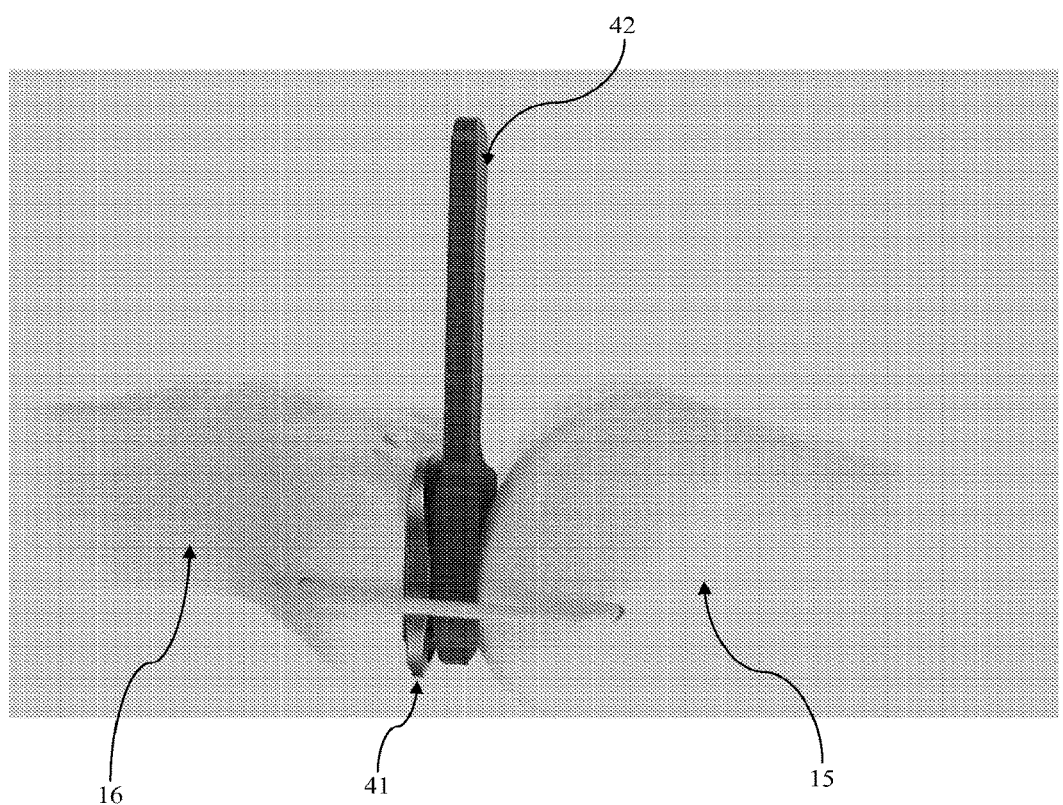
FIG. 7 is a perspective view of a knee in full extension with a tibial template in place for assessing if enough bone has been resected from the tibia.

The horizontal saw cut should be made with care so as to avoid damage to the soft tissues laterally, in particular the iliotibial tract and the posteriorly positioned lateral collateral ligament. The tibial plateau is removed and is then sized to the appropriate template 41. To confirm that enough bone has been resected from the tibia 16, the tibial template 41 should be inserted and the knee fully extended as shown in FIG. 7. If a No. 4 feeler gauge (or No. 3 in small women) 42 cannot be inserted in full extension the tibia 16 should be recut. Another of the differences between the operation to replace the medial compartment compared with the new operation to replace the lateral compartment is that to confirm enough bone has been resected from the tibia 16 in the lateral compartment the assessment is made in full extension, not 20° flexion as is the case on the medial side.

Once the tibia 16 has been resected and enough bone has been removed from the tibial plateau, the next step is to resect the femoral lateral condyle 60 to allow for the insertion of the femoral component 30. The aim of femoral preparation is to place the femoral component 30 as close to the anatomical position as possible. The size of the lateral femoral component 30 is selected using the same principles as is the medial component, i.e. is selected to be a similar size to that of the natural condyle.

Figure 8:
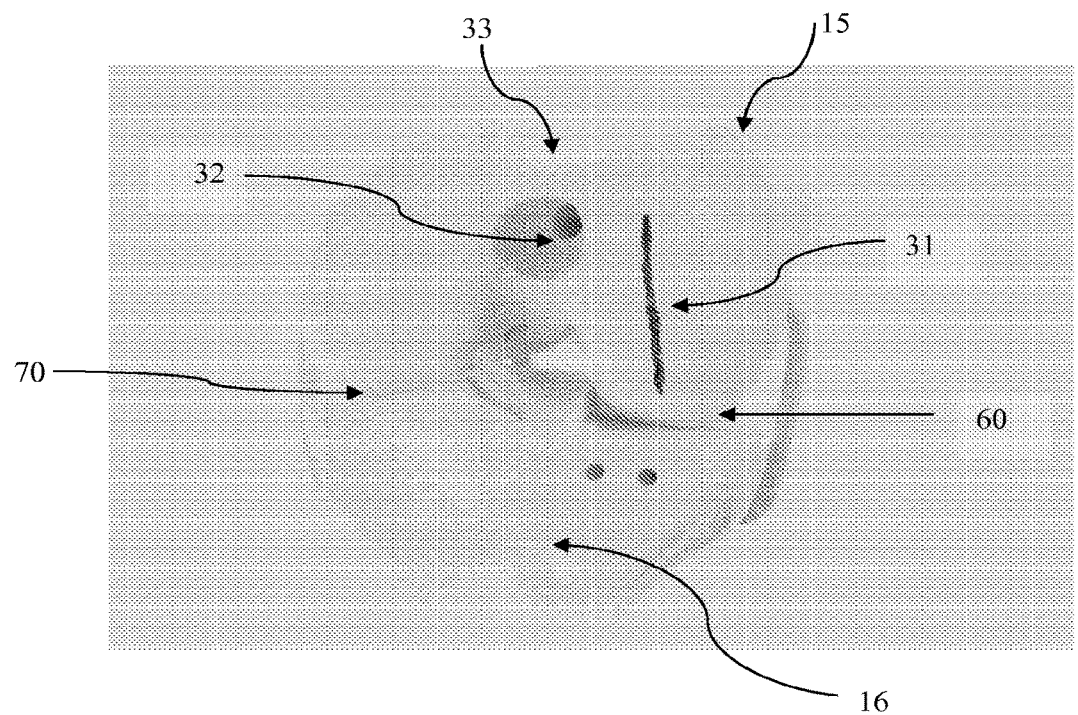
FIG. 8 is a perspective view of a knee with a line drawn down the centre of the lateral femoral condyle.

FIG. 8 shows a line 31 drawn down the centre of the lateral femoral condyle 60. An intramedullary rod (IM) (not shown) is inserted into a recess 32 about a centimeter anterior and a half centimeter lateral to the most anterolateral corner of the notch 33. The rod is left in place throughout the operation except when gaps are being measured. Care is taken not to damage the extension mechanism when flexing the knee 1; the patella 80 should be guided around the rod.

Figure 9:
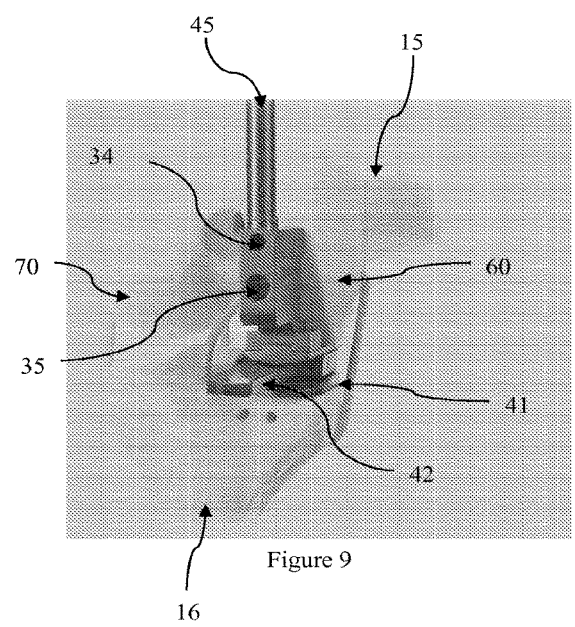
FIG. 9 is a perspective view of the knee with the femoral drill guide in place for drilling holes in the femur in accordance with the present invention.

FIG. 9 shows the tibial template 41, appropriate feeler gauge 42 and lateral/femoral drill guide 45, inserted into the gap between the lateral femoral condyle 60 and the articulating surface of the tibia 16. Alignment of the femoral drill guide 45 is fundamentally different to the medial side and can be disorientating due to the lateral condyle being less circular in cross section but more circular in the sagittal plane. The extramedullary alignment rod can therefore be used as an additional guide.

The position of the leg and guide are adjusted so that the IM rod is parallel to the drill guide 45 in both coronal and sagittal planes. The extramedullary rod should point to the femoral head and be parallel to the femur 15 in the sagittal plane. Achieving correct alignment is often difficult but 10° mal-alignment is acceptable. The mediolateral position of the drill guide 45 should be adjusted until it is central or just lateral to the centre of the lateral femoral condyle 60. This is best checked by seeing the line 31 drawn down the lateral femoral condyle 60 within the 6 mm drill hole 35 of the drill guide 45. The feeler gauge 42 will not be parallel to the wall of the tibial template 41 and may not be touching the tibial template 41.

Figure 10A:
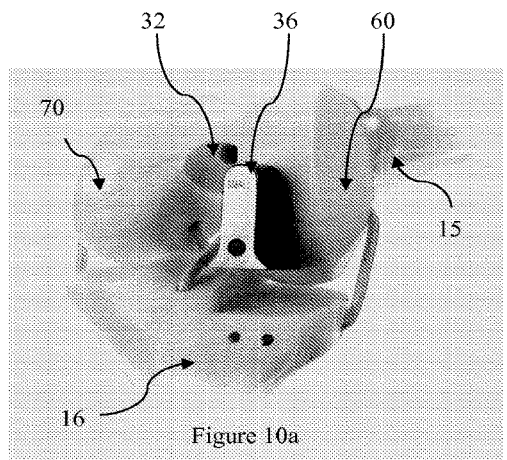
FIG. 10a is a perspective view of the knee with the posterior saw guide mounted on the lateral femoral condyle.

To prevent antero-lateral overhang of the femoral component 30 the drill guide 45 often needs to be positioned in slight internal rotation. Using the drill guide 45 two drill holes 34, 35 are made into the lateral femoral condyle 60. The drill guide 45 is then replaced by the posterior saw guide 36 as shown in FIG. 10a. The posterior saw guide 36 is used in the same manner as in the medial compartment to guide the saw cut such that the quantity of bone and cartilage removed equals the thickness of the posterior part of the implant. Any remnants of the posterior horn (at the back of the knee) of the meniscus are excised but the popliteus is not divided. It is the posterior horn of the meniscus that is more commonly injured.

Figure 10B:
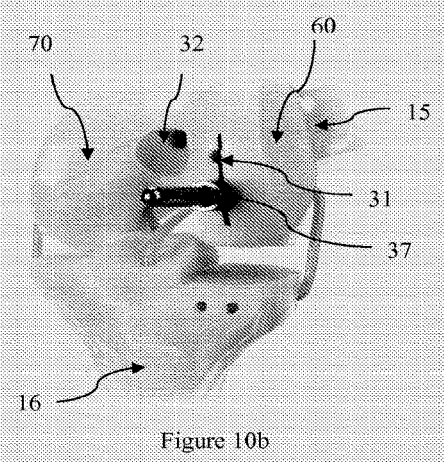
FIG. 10b is a perspective view of the knee with a '0' spigot in place for milling the femur.
Figure 10C:
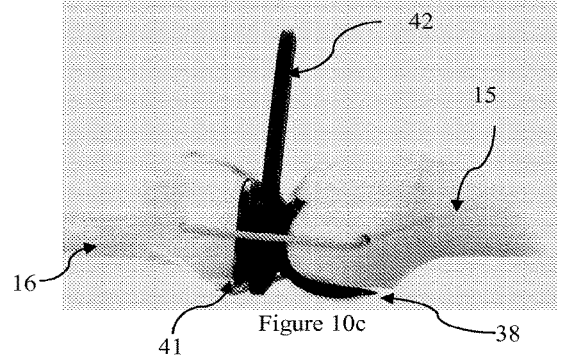
FIG. 10c is a perspective view of the knee in full extension with both femoral and tibial template components in place either side of a feeler gauge for assessing the flexion gap.

In flexion, the lateral ligaments are lax and the lateral structures are extensible, so the flexion gap cannot be measured accurately. Therefore, the femoral component 30 position cannot be determined by ligament balance. Instead, the aim is to position the femoral component 30 anatomically. This is achieved by milling the same thickness of cartilage and bone from the inferior surface of the femur to match the distal thickness of the implant. This is usually achieved by milling with a '4' spigot. Primary milling is undertaken with the '0' spigot 37 as shown in FIG. 10b. Trial components 38, 41 are inserted and the extension gap is measured with the knee fully extended using a feeler gauge 42 as shown in FIG. 10c. The tibial component is inserted then the knee extended.

Prior to using a '4' spigot and milling 4 mm from the distal femur 15 an assessment is made as to what effect this will have on the flexion gap. This is done by inserting a feeler gauge 42, 4 mm thicker than the measured extension gap. If this feeler gauge 42 is just gripped with the leg hanging dependant in flexion then milling with a '4' spigot should proceed. If the feeler gauge 42 is very tight, as may occur if there is a deep distal defect, then less bone should be removed. If the feeler gauge 42 is grossly loose then a '5' spigot may be used. In the vast majority of situations, a spigot higher than '5' should not be used as this will elevate the tibial joint line, and increase the risk of dislocation. Following secondary milling, trial components 38, 41 are inserted and an assessment of the gaps is made. It is likely that the flexion gap will be looser than the extension gap. If a varus load is applied, the flexion gap may open considerably. This is a manifestation of the loose lateral collateral ligament in flexion and is to be expected. Finally, with regard to the femur 15, bone is removed anteriorly and posteriorly on the femur 15 to prevent impingement.

Figure 11A:
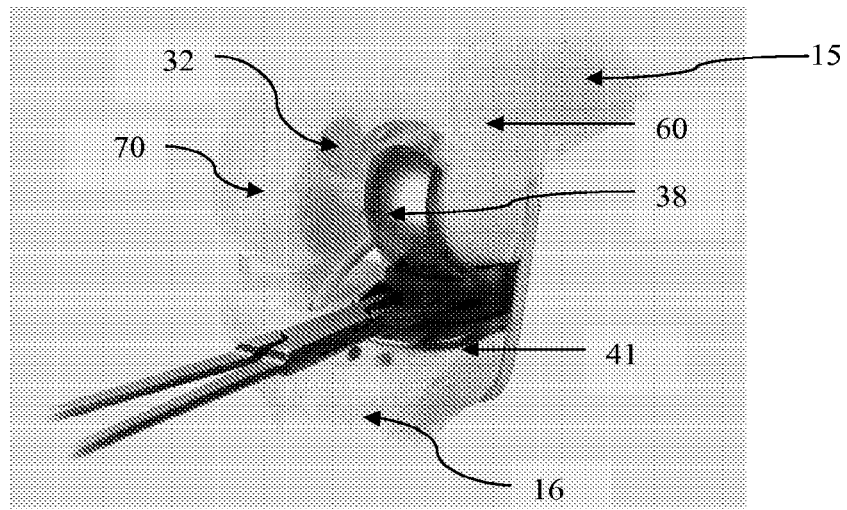
FIG. 11a shows a perspective view of the knee with a trial bearing in place between the femoral component and the tibial component.
Figure 11B:
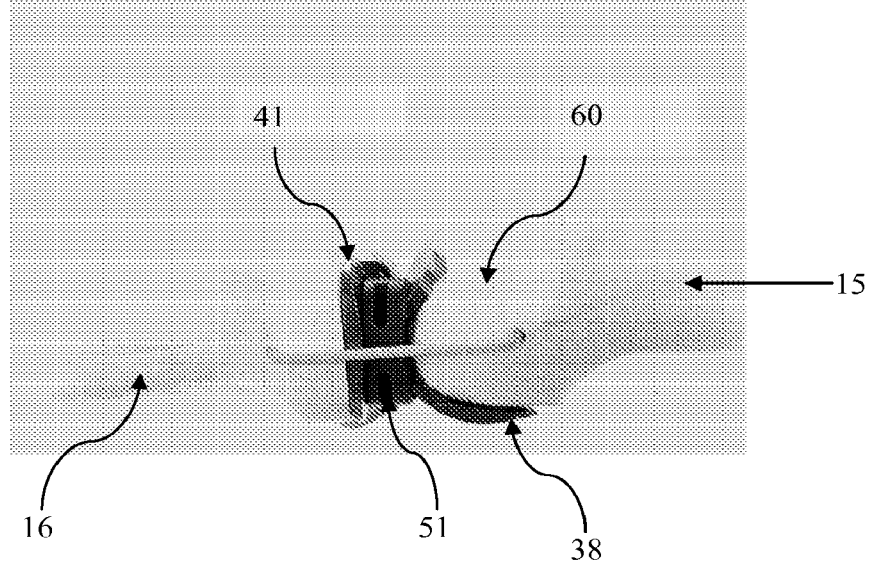
FIG. 11b shows a perspective view with the trial components and a trial bearing in place with the knee in full extension for a final assessment.

FIGS. 11a and 11b show a trial template bearing 51 inserted in between the femoral template 38 and the tibial template 41. The trial template bearing 51 thickness is selected in full extension. In this position, the trial template bearing 51 should be slightly lax. In flexion, the knee 1 may be very lax. This should be accepted. The medio-lateral position of the trial template bearing 51 should be assessed. If the trial template bearing 51 hits the wall, which is most likely to occur in full extension, the vertical tibial cut should be redone 1 to 2 mm more medial.

As described above, implant systems are affixed to the body by either cementing the prosthesis with bone cement or cementless such as biologic ingrowth or a combination of both of these. When using bone cement a special type of acrylic bone cement may be used to secure some or all of the implant components to the bone. However if using the cementless option the prosthesis is implanted into the bone without cement. These components have a special porous coating that allows tissue to grow into it for fixation. If using a combination of the two a surgeon may choose a combination of cement and cementless attachment, depending upon the implant components and the condition of the bone around the knee joint.

Once the final components 30, 40 and 50 have been chosen, a final assessment should be carried out prior to fixing the tibial component 40 and the femoral component 30 to their respective resected bone regions. Once final assessment is completed, care should be taken to ensure that there is nothing that might displace the mobile bearing 50 and cause a dislocation. If popliteus prevents the mobile bearing 50 from moving posteriorly it should be divided.

The tibial component 40 as described in FIG. 4 above has a projection or keel 14 for which further bone needs to be resected from the tibial plateau to accommodate the keel 14 of the tibial component 40. Once preparation of the surfaces with multiple drill holes has been completed the components 30, 40 are cemented in and excess cement is removed. A trial reduction is undertaken to determine the appropriate mobile bearing 50 thickness and to ensure there are no problems with the reconstruction. An appropriate mobile bearing 50 is one that is not tight in full extension. The definitive mobile bearing 50 is then inserted. This can usually be inserted from the front. If this is not possible consider using a thinner bearing. On the lateral side it is always better to leave the knee lax. If it is impossible to insert the mobile bearing 50 from the front, it can be inserted obliquely from an antero-lateral direction.

The knee must not be over stuffed resulting in the bearing being too tight. This will lead to pain and increase the risk of dislocation. It has been found that the best results are achieved in patients that have some residual valgus.

Orthopedic surgery or orthopedics (also spelled orthopaedics) is the branch of surgery concerned with conditions involving the musculoskeletal system. In order to provide the orthopedic surgeon with the tools and equipment required to perform a knee implant in particular, a lateral unicondylar knee implant a set or collection of tools, supplies, and instructional matter, etc., for the specific purpose of implanting a lateral unicondylar knee prosthesis is provided. This kit is designed to give an orthopedic surgeon the tools needed to perform the implant. The kit may include but is not limited to: (a) a set of femoral components; (b) a set of tibial components; (c) a set of mobile bearing components; (d) a set of feeler gauges for determining correct sizing of components; and (e) a set of instructions for performing a lateral unicondylar knee implant surgery.

Each set is further broken down into specific components required for the implant surgery, and may include the following:

(a) a set of femoral components including:
 (i) at least one femoral drill guide;
 (ii) at least one femoral prosthetic component;
 (iii) at least one femoral prosthetic template component; and
 (iv) a femoral instrument set.
(b) a set of tibial components including:
 (i) at least one tibial prosthetic component;
 (ii) at least one tibial prosthetic template component;
 (iii) a tibial impactor; and
 (iv) a tibial instrument set.
(c) a set of bearing components including:
 (i) at least one mobile bearing member;
 (ii) at least one mobile bearing template member; and
 (iii) a bearing insert/removal tool.
(d) a set of feeler gauges for determining correct sizing of components; and
(e) a set of instructions for performing a lateral unicondylar knee implant surgery.

As surgery is carried out under sterile conditions all of the equipment is placed into a domed lateral sterilisation case to allow for easy sterilisation of all components required in the kit.

Figure 12:
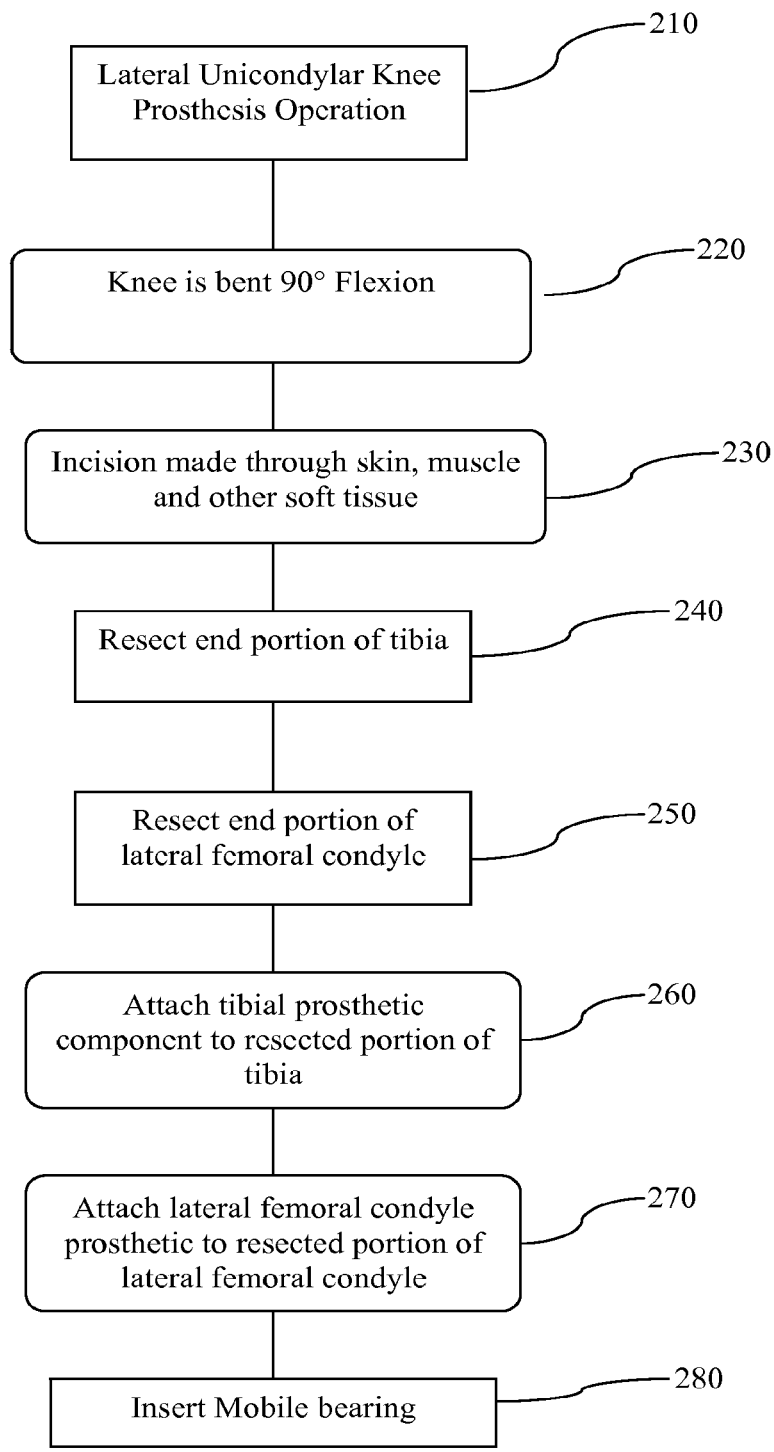
FIG. 12 is a flowchart illustrating the method in accordance with an embodiment of the present invention.
Figure 13:
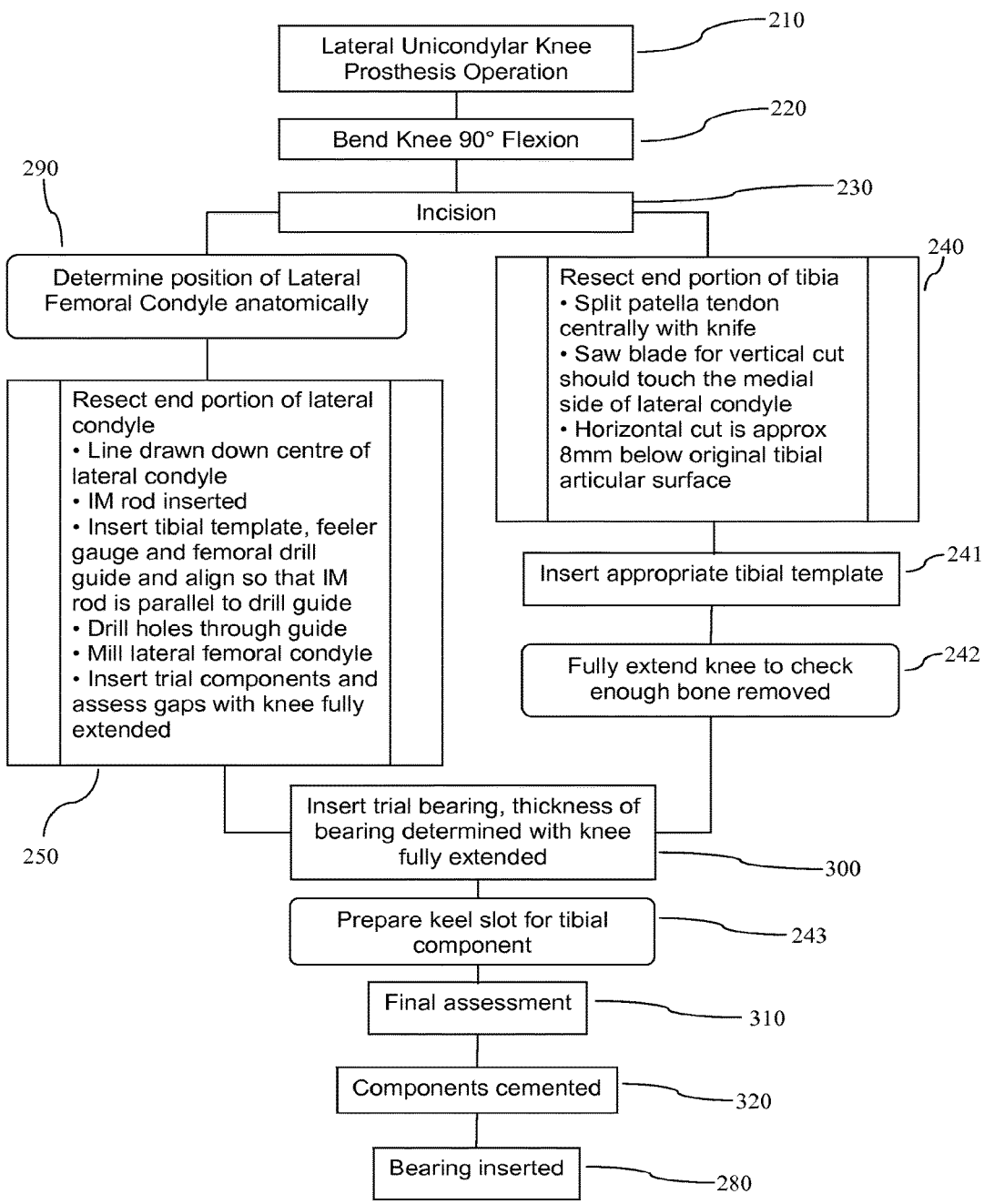
FIG. 13 shows a detailed flow chart illustrating the method in accordance with an embodiment of the present invention.

Finally with reference to FIGS. 12 and 13 the method of implanting a lateral unicondylar knee prosthesis 210 in a lateral articulating portion of a femur 15 having a lateral condyle 60 for engagement with a tibia 16 is described. Firstly, in flexion, the lateral collateral ligament (LCL) is slack whereas the medial collateral ligament (MCL) is tight. Therefore, it is not possible to determine the position of the lateral femoral condyle 60 from ligament balance, as is done in operations to replace the medial compartment (discussed in more detail latter). Therefore with the knee bent to approximately 90° flexion 220, an incision 230 is made through the skin, muscle and other soft tissue.

The method is now split into two distinct and different phases (resect tibia) 240 and (resect lateral femoral condyle) 250. The end portion of the tibia is resected 240 by firstly splitting the patella tendon centrally with a knife. A vertical saw cut is then made through the patella tendon with the knee flexed to 90°. The saw blade should touch the medial side of the lateral condyle 60. The two landmarks, the centre of the tendon and the medial side of the lateral condyle 60 define the position of the cut and ensure it is adequately internally rotated. The saw cut will usually be at the correct depth when its upper edge is level with the bone surface.

A horizontal saw cut is then made, where the aim is for the horizontal cut to be approximately 8 mm below the original tibial articular surface. If the site of the original surface can not be estimated, the cut should be approximately 2 or 3 mm below the eburnated bone. A tibial template 41 is then inserted 241 and with the knee 1 fully extended and an assessment 242 is made to confirm that enough bone has been resected from the tibia 16.

The next step 250 is to resect the lateral femoral condyle 60 to allow for the insertion of the femoral component 30. The aim of femoral preparation is to place the femoral component 30 as close to the anatomical position 290 as possible. The size of the lateral femoral component 30 is selected using the same principles as is the medial component and the lateral femoral condyle 60 is resected as described above with reference to FIGS. 8 to 11.

Trial components 38, 41 are inserted 300 and the extension gap is measured with the knee fully extended. A trial reduction is undertaken to determine the appropriate mobile bearing 50 thickness and to ensure there are no problems with the reconstruction. An appropriate mobile bearing 50 is one that is not tight in full extension. The tibial component 40 as described in FIG. 4 above has a projection or keel 14 for which further bone needs to be resected 243 from the tibial plateau to accommodate the keel 14 of the tibial component 40.

A final assessment 310 is then performed to ensure all gaps are acceptable and that there is free movement of the joint. The tibial prosthetic component 40 is then attached 260 to the resected portion of the tibia and the lateral femoral condylar component 40 are also attached 270 to the resected portion of the lateral condyle. Both components 30, 40 are then cemented 320 to their respective bones. Finally a mobile bearing 50 is inserted 280.

Although the present invention has been illustrated and described with respect to exemplary embodiment thereof, it should be understood by those skilled in the art that the foregoing and various other changes, omission and additions may be made therein and thereto, without departing from the scope of the invention. Therefore the present invention should not be understood as limited to the specific embodiment set out above but to include all possible embodiments that can be embodied within a scope encompassed and equivalent thereof with respect to the features set out in the appended claims.

What is claimed is:

1. A method of implanting a lateral unicondylar knee prosthesis in a lateral articulating portion of a femur having a lateral condyle for engagement with a lateral tibia, the method comprising the steps of:

bending a patient's knee such that the knee is not in full extension;

making an incision through the skin, muscle, and other soft tissue until the damaged bone surfaces are exposed;

resecting an end portion of the lateral tibia but leaving other portions of the tibia including a medial tibia unresected;

resecting an end portion of the lateral femoral condyle but leaving other portions of the femur including a medial femoral condyle unresected;

attaching a tibial prosthetic component to the resected end portion of the lateral tibia;

attaching a lateral femoral condyle prosthetic component to the resected end portion of the lateral femoral condyle;

determining an appropriate thickness of a mobile bearing member with the knee only in full knee extension so that a lateral collateral ligament is tight rather than determining the appropriate thickness of the mobile bearing with the knee in knee flexion when the lateral collateral ligament is slack wherein the appropriate thickness of the mobile bearing member is determined by sizing a tibial template component and sizing a lateral femoral template component with the knee fully extended and sizing a mobile bearing template member for insertion between the tibial template component and the lateral femoral template; and inserting the mobile bearing member having the determined appropriate thickness between the tibial prosthetic component and the lateral femoral prosthetic component.

2. The method according to claim 1, wherein the position of the lateral femoral condyle is determined anatomically with reference to the femur.

3. The method according to claim 1, wherein the step of resecting the end portion of the tibia comprises:
sawing vertically a cut through the centre of a patella tendon positioned in line with the medial side of the lateral femoral condyle; and
sawing horizontally a cut that removes bone to accommodate the tibial prosthetic component and the mobile bearing member with the knee in full extension.

4. The method according to claim 3, wherein sawing horizontally further comprises removing bone to approximately 8 mm below the original tibial articular surface or 2 to 3 mm below the eburnated bone of the tibia.

5. The method according to claim 1, wherein the tibial prosthetic component comprises a smooth articular surface and a bone contacting surface opposite the articular surface.

6. The method according to claim 5, wherein the smooth articular surface is formed in a convex shape.

7. The method according to claim 5, wherein the bone contacting surface opposite the articular surface further comprises a projection extending from the bone contacting surface.

8. The method according to claim 7, wherein the step of attaching the tibial prosthetic component comprises:
resecting the bone to accommodate the projection extending from the bone contacting surface; and
cementing the tibial prosthetic component to the tibia.

9. The method according to claim 7, wherein the step of attaching the tibial prosthetic component comprises:
resecting the bone to accommodate the projection extending from the bone contacting surface; and
attaching a cementless tibial prosthetic component to the tibia.

10. The method according to claim 1, wherein the femoral prosthetic component comprises a smooth articular surface and a bone contacting surface opposite the articular surface.

11. The method according to claim 10, wherein the smooth articular surface is formed in a convex shape.

12. The method according to claim 10, wherein the bone contacting surface opposite the articular surface further comprises a spigot extending from the bone contacting surface.

13. The method according to claim 10, wherein the step of attaching the lateral femoral prosthetic component comprises:
cementing the lateral femoral prosthetic component to the femur.

14. The method according to claim 10, wherein the step of attaching the lateral femoral prosthetic component comprises:
attaching a cementless lateral femoral prosthetic component to the femur.

15. The method according to claim 1 wherein the mobile bearing member is a biconcave bearing having a first bearing surface which articulates with the smooth articular surface of the tibial prosthetic component and a second bearing surface which articulates with the smooth articular surface of the femoral prosthetic component.

16. The method according to claim 1, wherein the tibial prosthetic component, the femoral prosthetic component and the mobile bearing member are made of a material selected from the group of titanium, titanium alloy, cobalt chrome alloy, ceramic, biocompatible composite, polymer, niobium, and steel alloy.

17. A method of implanting a lateral unicondylar knee prosthesis in a lateral articulating portion of a femur having a lateral condyle for engagement with a tibia, the method comprising the steps of:
bending a patient's knee such that the knee is not in full extension;
making an incision through the skin, muscle, and other soft tissue until the damaged bone surfaces are exposed;
resecting an end portion of the lateral tibia;
resecting an end portion of the lateral femoral condyle;
attaching a tibial prosthetic component to the resected end portion of the tibia;
attaching a lateral femoral condyle prosthetic component to the resected end portion of the lateral femoral condyle;
determining an appropriate thickness of a mobile bearing member with the knee in full extension so that a lateral collateral ligament is tight in full knee extension and is slack in knee flexion; and
inserting the mobile bearing member having the determined appropriate thickness between the tibial prosthetic component and the femoral prosthetic component,
wherein the step of resecting the end portion of the lateral femoral condyle comprises:
drilling a hole in a notch between the lateral femoral condyle and the medial femoral condyle to accommodate an intramedullary rod;
inserting a lateral femoral drill guide;
adjusting the leg and the lateral femoral drill guide to be parallel to the intramedullary rod;
drilling two holes through the lateral femoral drill guide;
attaching a posterior saw guide to the lateral femoral compartment; and
milling the bone from the lateral femoral condyle in both anterior and posterior directions.

18. A method of sizing a lateral unicondylar knee prosthesis for implantation in a lateral articulating portion of a femur having a lateral condyle for engagement with a lateral tibia, the method comprising the steps of:
bending a patient's knee such that the knee is not in full extension;
making an incision through the skin, muscle, and other soft tissue until the damaged bone surfaces are exposed;
resecting an end portion of the lateral tibia but leaving other portions of the tibia including a medial tibia unresected;
inserting a lateral tibial template component and fully extending the knee to confirm sufficient tibial resection of the lateral tibia;
resecting an end portion of the lateral femoral condyle but leaving other portions of the femur including a medial femoral condyle unresected;
inserting a lateral femoral template component and fully extending the knee to confirm sufficient femoral resection of the lateral femoral condyle;
inserting a mobile bearing template member between the lateral tibial template component and the lateral femoral template component and fully extending the knee to full knee extension;
determining an appropriate mobile bearing template thickness only when the knee is in full knee extension so that a lateral collateral ligament is tight rather than determining the appropriate thickness of the mobile bearing with the knee in knee flexion when the lateral collateral ligament is slack; and sizing the prosthesis based on the lateral tibial template component, the lateral femoral template component, and the mobile bearing template member.

19. The method of claim 18, wherein the step of resecting the end portion of the lateral tibia comprises:

sawing vertically a cut through the centre of a patella tendon positioned in line with the medial side of the lateral femoral condyle; and sawing horizontally a cut that removes bone to accommodate the tibial prosthetic component and the mobile bearing member with the knee in full extension.

* * * * *